(12) United States Patent
Griffin et al.

(10) Patent No.: US 7,060,703 B2
(45) Date of Patent: Jun. 13, 2006

(54) INDOLINONE DERIVATIVES

(75) Inventors: John H. Griffin, Atherton, CA (US); Roger Briesewitz, Mountain View, CA (US); Jonathan W. Wray, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 49 days.

(21) Appl. No.: 10/691,094

(22) Filed: Oct. 22, 2003

(65) Prior Publication Data

US 2004/0198804 A1 Oct. 7, 2004

Related U.S. Application Data

(62) Division of application No. 10/327,385, filed on Dec. 20, 2002, now Pat. No. 6,686,362.

(60) Provisional application No. 60/343,746, filed on Dec. 27, 2001, provisional application No. 60/343,813, filed on Dec. 27, 2001.

(51) Int. Cl.
*A61K 31/496* (2006.01)
*C07D 403/10* (2006.01)

(52) U.S. Cl. ............. 514/254.01; 544/144; 514/254.09
(58) Field of Classification Search ........... 514/254.09, 514/254.01; 544/144
See application file for complete search history.

(56) References Cited

U.S. PATENT DOCUMENTS

| 6,130,239 A * | 10/2000 | Chen et al. .................. 514/414 |
| 6,258,812 B1 | 7/2001 | Bold et al. |
| 6,395,734 B1 | 5/2002 | Tang et al. |
| 2004/0045044 A1 | 3/2004 | Briesewitz et al. |

FOREIGN PATENT DOCUMENTS

| WO | WO 96/40116 | 12/1996 |
| WO | WO 99/61422 | 12/1999 |
| WO | WO 00/38519 | 7/2000 |
| WO | WO 00/73297 A1 | 12/2000 |
| WO | WO 01/16130 A1 | 3/2001 |
| WO | WO 01/25238 A2 | 4/2001 |
| WO | WO 01/27080 A2 | 4/2001 |
| WO | WO 01/27081 A1 | 4/2001 |
| WO | WO 01/42243 A2 | 6/2001 |
| WO | WO 01/60814 A2 | 8/2001 |
| WO | WO 02/02551 A1 | 1/2002 |
| WO | WO 02/16351 A1 | 2/2002 |
| WO | WO 02/055517 A2 | 7/2002 |

OTHER PUBLICATIONS

Awada, A. et al, The pipeline of new anticancer agents for breast cancer treatment in 2003, Critical Reviews in Oncology/Hematology, vol. 48, pp. 45-63.*

Nahta, R. et al., Novel pharmacological approaches in the treatment of breast cancer, Expert Opin. Investigational IDRugs, vol. 12(6), pp. 909-921.*

Nahta, R. et al., "Growth Factor Receptors in Breast Cancer" Potential for Therapeutic Intervention, The Oncologist, vol. 8, pp. 5-17.*

Barton, J. et al. Urology (Aug. 2001), vol. 58, Suppl. A2, pp. 155-155.*

"Avastin-Tarceva Combo Provides 'One-Two' Punch Against Lung Cancer," Science Daily (Jun. 7, 2004).*

Goldman, B. "For Investigational Targeted Drugs, Combination Trials Pose Challenges," J. National Cancer Institute (2003), vol. 95 (23), pp. 1744-1746.*

Robinson, D. et al, "The protein kinase family of the human genome," Oncogene (2000), vol. 19, pp. 5548-5557.*

U.S. Food & Drug Administration, "FDA Statement on Iressa," released Dec. 17, 2004, p. 1.*

Abrams et al., Abstract: Su6668, a Broad Spectrum Angiogenesis Inhibitor, Is Active in Diverse Models of Tumor Growth and Metastasis, From the Proceedings of the AACR, vol. 42, Mar. 2001; Copyright 2001 by the American Association for Cancer Research; Online Publication Date: Feb. 27, 2001.

Abrams et al., "SU6668, a Broad Spectrum Angiogenesis Inhibitor is Active in Diverse Models of Tumor Growth and Metastasis", Presented at AACR, 92nd Annual Meeting, Mar. 24-28, 2001, Ernest N. Morial Convention Center, New Orleans, LA.

Fiedler et al., "Abstract 1148:A Phase II Study With SU55416 in Patients With c-kit Positive AML", Presented at ASCO 2001, American Society of Clinical Oncology, May 12-15, 2001, Moscone Center, San Francisco, California.

(Continued)

*Primary Examiner*—Kamal A. Saeed
*Assistant Examiner*—Janet L. Coppins
(74) *Attorney, Agent, or Firm*—Jeffery Hagenah; Roberta P. Saxon; Joyce G. Cohen

(57) ABSTRACT

Compounds of formula (I)

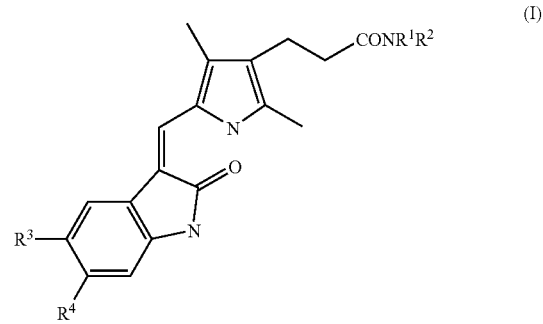

in which $R^1$, $R^2$, $R^3$ and $R^4$ have the meanings given in the specification, are receptor tyrosine kinase inhibitors useful in the treatment of proliferative disorders, such as cancer.

6 Claims, No Drawings

OTHER PUBLICATIONS

Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types" Cancer Research, vol. 59, pp. 99-106 (Jan. 1, 1999).

Laird et al., "SU6668 Is a Potent Antiangiogenic and Antitumor Agent That Induces Regression of Established Tumors[1]", Cancer Research, vol. 60, pp. 4152-4160 (Aug. 1, 2000).

Levis et al., "A FLT3 tyrosine kinase inhibitor is selectively cytotoxis to acute myeloid leukemia blasts harboring FLT3 internal tandem duplication mutations", Blood, vol. 98, No. 3, pp. 885-887 (Aug. 1, 2001).

O'Farrell et al., Abstract: "[497]SUGEN Compounds SU5416 and SU11248 Inhibit Flt3 Activity:Therapeutic Applications in AML.", Presented at American Society of Hematology Meeting, Dec. 7-11, 2001, Orlando, Florida (1 sheet).

Pandey et al., "Identification of Orally Active, Potent, and Selective 4-Piperazinylquinazolines as Antagonists of the Platelet-Derived Growth Factor Receptor Tyrosine Kinase Family", J. Med. Chem, vol. 45, pp. 3772-3793 (2002).

Shaheen et al., "Tyrosine Kinase Inhibition of Multiple Angiogenic Growth Factor Receptors Improves Survival in Mice Bearing Colon Cancer Liver Metastases by Inhibition of Endothelial Cell Survival Mechanisms[1]", Cancer Research, vol. 61, pp. 1464-1468 (Feb. 15, 2001).

Sun et al., "Design, Synthesis, and Evaluations of Substituted 3-[3- or 4-Carboxyethylpyrrol-2-yl)methylidenyl]indolin-2-ones as Inhibitors of VEGF, FGF, and PDGF Receptor Tyrosine Kinases", J. Med. Chem., vol. 42, pp. 5120-5130 (1999).

Sun et al., Identification of Substituted 3-[4,5,6,7-Tetrahydro-1$H$-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases J. Med. Chem., vol. 43, pp. 2655-2663 (2000).

Sun et al., "Synthesis and Biological Evaluations of 3-Substituted Indolin-2-ones: A Novel Class of Tyrosine Kinase Inhibitors That Exhibit Selectivity toward Particular Receptor Tyrosine Kinases", J. Med. Chem., vol. 41, pp. 2588-2603 (1998).

Traxler et al., "Protein tyrosine kinase Inhibitors in cancer treatment", Exp. Opin. Ther. Patents, vol. 7, No. 6, pp. 571-588 (1997).

Wild et al., Abstract: "SU5416 and SU6668 Inhibit Tyrosine Kinase Mediated Survival Signals and Induce Apoptosis in Myeloid Leukemia Cells", From the Proceedings of the AACR, vol. 42, Mar. 2001; Copyright 2001 by the American Association for Cancer Research; Online Publication Date: Feb. 27, 2001 (1 sheet).

Yee et al., Abstract: "SU5416 Inhibits wild-type and activated mutant FLT3 signaling in leukemia cells", Copyright 2001 American Association for Cancer Research; Proceedings of the AACR-NC1-EORTC International Conference; Published as a Supplement to Clinical Cancer Research, vol. 7, No. 11, Nov. 2001 (1 sheet).

Yee et al., "SU5416 and SU5614 inhibit kinase activity of wild-type and mutant FLT 3 receptor tyrosine kinase", Blood, vol. 100, No. 8, pp. 2941-2949 (Oct. 15, 2002).

U.S. Appl. No. 11/008,746, filed Dec. 9, 2004, Briesewitz.

Aiello et al., "Suppression of retinal neovascularization *in vivo* by inhibition of vascular endothelial growth factor (VEGF) using soluble VEGF-receptor chimeric proteins", Proc. Natl. Acad. Sci USA, vol. 92, pp. 10457-10461, Nov. 1995.

Drevs et al., "Effects of PTK787/ZK 222584, a Specific Inhibitor of Fascular Endothelial Growth Factor Receptor Tyrosine Kinases, on Primary Tumor, Metastasis, Vessel Density, and Blood Flow in a Murine Renal Cell Carcinoma Model", Cancer Research 60, pp. 4819-4824 (Sep. 1, 2000).

Mendel et al., "*In Vivo* Antitumor Activity of SU11248, a Novel Tyrosine Kinase Inhibitor Targeting Vascular Endothelial Growth Factor and Platelet-derived Growth Factor Receptors: Determination of a Pharmacokinetic/Pharmacodynamic Relationship", Clinical Cancer Research, vol. 9, pp. 327-337 (Jan. 2003).

Wood, "Inhibition of Vascular Endothelial Growth Factor (VEGF) as a Novel Approach for Cancer Therapy", Medicina (Buenos Aires) 60 (Supl. II), pp. 41-47 (2000).

Zwick et al., "Receptor tyrosine kinase signalling as a target for cancer intervention strategies", Endocrine-Related Cancer, vol. 8, pp. 161-173 (2001).

* cited by examiner

INDOLINONE DERIVATIVES

CROSS REFERENCE TO RELATED APPLICATIONS

This application is a divisional of U.S. application Ser. No. 10/327,385, filed Dec. 20, 2002, now U.S. Pat. No. 6,686,362 which claims the benefit of U.S. Provisional Application No. 60/343,746, filed Dec. 27, 2001 and U.S. Provisional Application No. 60/343,813, filed Dec. 27, 2001, the entire disclosures of which are incorporated herein by reference.

FIELD OF THE INVENTION

The present invention relates to novel indolinone derivatives useful as pharmaceuticals, to processes for preparing the compounds, to intermediates useful in the preparation of the compounds, to pharmaceutical compositions comprising the compounds, and to the use of the compounds as pharmaceuticals.

BACKGROUND OF THE INVENTION

WO 96/40116 disclose that certain pyrrole substituted 2-indolinone derivatives are receptor tyrosine kinase inhibitors useful in the treatment of conditions responsive to receptor tyrosine kinase inhibitors, for example proliferative disorders such as cancer. A preferred compound, disclosed on page 17, is 3-(2,3-dimethylpyrrol-5-yl)methylene]-2-indolinone, also known as SU5416. Unfortunately, this compound has been found to exhibit poor solubility in water and low bioavailability upon oral and intravenous administration.

WO 99/61422 discloses further pyrrole substituted 2-indolinone derivatives as receptor tyrosine kinase inhibitors. A preferred compound, disclosed as compound 5 on page 214, is 3-[2,4-dimethyl-5-(2-oxo-1,2-dihydroindol-3-ylidenemethyl)-1H-pyrrol-3-yl]propionic acid, also known as SU6668. This compound has been found to possess superior oral activity to SU5416, but has been reported to lack the ability of that compound to inhibit the receptor tyrosine kinase Flt-3 (Abstract 497, Anne-Marie O'Farrell et al., America Society of Hematology Meeting, Orlando, Fla., USA, Dec. 7–11, 2001). Flt-3 is an important target for a tyrosine kinase inhibitor, especially for the treatment of Acute Myeloid Leukemia (AML), because about 30% of AML patients have been found to possess mutant forms of Flt-3 which lead to constitutive tyrosine phosphorylation of Flt-3 (Levis et al., *Blood*, 1 Aug., 2001, Vol. 98. No. 3, pp 885–887).

WO 01/60814 discloses pyrrole substituted 2-indolinone derivatives bearing certain amido substituents directly attached to the pyrrole ring as receptor tyrosine kinase inhibitors.

WO 02/055517 discloses indolinones substituted with aryl substituents at the 4 position which exhibit protein kinase modulating ability.

WO 01/42243 discloses that certain compounds containing two or more pyrrole substituted 2-indolinone groups covalently linked together through the 3 position on each pyrrole by one or more linker groups are also useful as receptor tyrosine kinase inhibitors.

Nonetheless, in view of the severity of conditions responsive to receptor tyrosine kinase inhibitors and of the recent identification of specific kinase inhibitor targets, a need exists for new receptor tyrosine kinase inhibitors with diverse properties.

SUMMARY OF THE INVENTION

Pyrrole substituted 2-indolinone derivatives bearing certain carboxamidoethyl groups at the 4 position on pyrrole have now been found that are inhibitors of receptor tyrosine kinases with particularly desirable properties.

Accordingly, the present invention provides a compound of formula (I):

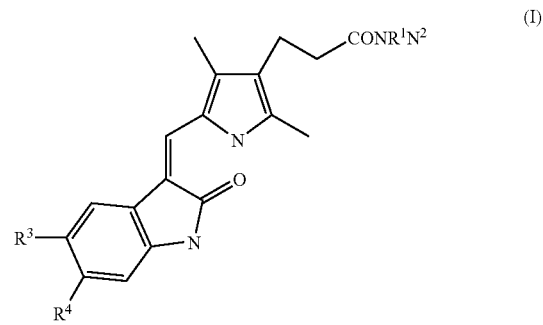

in which:

(i) $R^1$ represents a hydrogen atom or a (1–4C)alkyl group; and $R^2$ represents a group of formula -$A^1$-$NR^5R^6$ in which each of $R^5$ and $R^6$ independently represents a hydrogen atom or a (1–4C)alkyl group and $A^1$ represents $(CH_2)_m$, $(CH_2)_n$-$A^2$-$(CH_2)_p$ or $(CH_2CH_2O)_qCH_2CH_2$ in which m is an integer of from 2 to 10, each of n and p is an integer of from 1 to 6, $A^2$ is CH=CH, phenylene, biphenylene, cyclohexylene or piperazinylene and q is 1, 2 or 3;

(ii) $R^1$ and $R^2$ together represent -$A^3$-$NR^7$-$A^4$- in which each of $A^3$ and $A^4$ independently represents $(CH_2)_r$ or $(CH_2CH_2O)_sCH_2CH_2$ in which r is an integer of from 2 to 6, s is 1, 2 or 3, and $R^7$ represents a hydrogen atom or a (1–4C)alkyl group;

(iii) $R^1$ and $R^2$ together with the nitrogen atom to which they are attached represent a piperidinyl group, which piperidinyl group bears a substituent of formula -$A^5$-$R^8$ at the 4 position, in which $A^5$ represents (1–4C)alkylene and $R^8$ represents piperidin-4-yl; or (iv) $R^1$ and $R^2$ together with the nitrogen atom to which they are attached represent a pyrrolidinyl, piperidinyl or morpholino group; and $R^3$ and $R^4$ each independently represents a hydrogen atom, a halogen atom, a (1–4C)alkyl group, a (1–4C)alkoxy group, a phenyl group which is unsubstituted or substituted by one or two substituents selected independently from a halogen atom, a (1–4C)alkyl group and a (1–4C)alkoxy group, a group of formula $R^9S(O)_2NR^{10}$—, a group of formula $R^{11}N(R^{12})S(O)_2$—, a group of formula $R^{13}C(O)N(R^{14})$— or a group of formula $R^{15}N(R^{16})C(O)$— in which each of $R^9$, $R^{11}$, $R^{13}$ and $R^{15}$ independently represents a (1–4C)alkyl group or a phenyl group which is unsubstituted or substituted by one or two substituents selected independently from a halogen atom, a (1–4C)alkyl group and a (1–4C)alkoxy group, and each of $R^{10}$, $R^{12}$, $R^{14}$ and $R^{16}$ independently represents a hydrogen atom or a (1–4C)alkyl group;

or a pharmaceutically-acceptable salt thereof.

Compounds of formula (I) have been found to be potent and selective inhibitors of one or more of the receptor tyrosine kinases PDGFR (platelet-derived growth factor), c-Kit, VEGFR (vascular endothelial growth factor) and Flt-3 in whole cell assays.

The invention also provides compounds of formula (Ia):

(Ia)

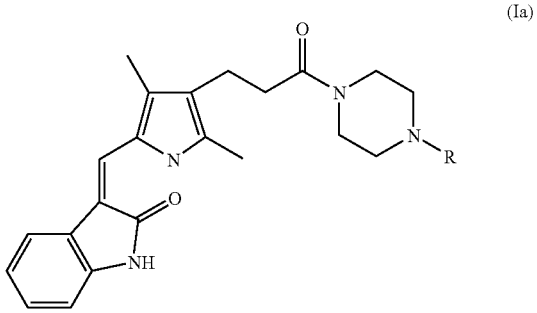

wherein R is hydrogen, methyl, or ethyl;
or a pharmaceutically-acceptable salt thereof.

The invention also provides pharmaceutical compositions comprising a compound of the invention or a pharmaceutically-acceptable salt thereof and a pharmaceutically-acceptable carrier.

In addition, the invention provides a method of treating a condition responsive to a tyrosine kinase inhibitor, the method comprising administering to a patient in need of treatment an effective amount of a compound of the invention.

Further, the invention provides a compound of the invention as described herein for use in medical therapy, as well as the use of a compound of the invention in the manufacture of a formulation or medicament for treating a disease or condition responsive to a tyrosine kinase inhibitor.

DETAILED DESCRIPTION

The present invention provides novel pyrrole substituted 2-indoline derivatives which are substituted at the 4 position of the pyrrole ring with carboxamidoethyl substituents.

As used herein, the terms alkyl and alkylene refer to a branched or unbranched group. However, the names of specific groups, such as ethyl, ethylene, propyl, propylene, butyl or butylene, signify unbranched groups or radicals, unless indicated otherwise, such as prop-2-yl. Examples of alkyl groups are methyl, ethyl, propyl, prop-2-yl, and butyl. Examples of alkylene groups are methylene, ethylene, propylene and butylene.

The term halogen atom includes fluorine, chlorine and bromine.

The term "therapeutically effective amount" refers to an amount sufficient to effect treatment when administered to a patient in need of treatment.

The term "treatment" as used herein refers to the treatment of a disease or medical condition in a patient, such as a mammal (particularly a human), and includes:
(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The term "pharmaceutically-acceptable salt" refers to a salt prepared from a base or acid which is acceptable for administration to a patient, such as a mammal. Such salts can be derived from pharmaceutically-acceptable inorganic or organic acids.

Salts derived from pharmaceutically-acceptable acids include acetic, benzenesulfonic, benzoic, camphosulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid) and the like. Particularly preferred are salts derived from fumaric, hydrobromic, hydrochloric, acetic, sulfuric, phosphoric, methanesulfonic, p-toluenesulfonic, xinafoic, tartaric, citric, malic, maleic, succinic, and benzoic acids.

One preferred sub-group of compounds of formula (I) is that in which:

(i) $R^1$ represents a hydrogen atom or a (1–4C)alkyl group; and $R^2$ represents a group of formula $-A^1-NR^5R^6$ in which each of $R^5$ and $R^6$ independently represents a hydrogen atom or a (1–4C)alkyl group and $A^1$ represents $(CH_2)_m$, $(CH_2)_n$-$A^2$-$(CH_2)_p$ or $(CH_2CH_2O)_qCH_2CH_2$ in which m is an integer of from 2 to 10, each of n and p is an integer of from 1 to 6, $A^2$ is CH=CH, phenylene, biphenylene, cyclohexylene or piperazinylene and q is 1, 2 or 3;

(ii) $R^1$ and $R^2$ together represent $-A^3-NR^7-A^4-$ in which each of $A^3$ and $A^4$ independently represents $(CH_2)_r$ or $(CH_2CH_2O)_sCH_2CH_2$ in which r is an integer of from 2 to 6, s is 1, 2 or 3, and $R^7$ represents a hydrogen atom or a (1–4C)alkyl group; or (iii) $R^1$ and $R^2$ together with the nitrogen atom to which they are attached represent a piperidinyl group, which piperidinyl group bears a substituent of formula $-A^5-R^8$ at the 4 position, in which $A^5$ represents (1–4C)alkylene and $R^8$ represents piperidin-4-yl.

Compounds belonging to the above preferred sub-group have been found to exhibit good solubility in water and good absorption on oral administration.

In this sub-group of compounds, preferably (i) $R^1$ represents a hydrogen atom or a (1–4C)alkyl group; and $R^2$ represents a group of formula $-A^1-NR^5R^6$ in which each of $R^5$ and $R^6$ independently represents a hydrogen atom or a (1–4C)alkyl group and $A^1$ represents $(CH_2)_m$, $(CH_2)_n$-$A^2$-$(CH_2)_p$ or $(CH_2CH_2O)_qCH_2CH_2$ in which m is an integer of from 2 to 10, each of n and p is an integer of from 1 to 6, $A^2$ is CH=CH, phenyl-1,3-ene, phenyl-1,4-ene, biphenyl-2,2'-ene, cyclohex-1,3-ylene or piperazin-1,4-ylene and q is 1, 2 or 3;

(ii) $R^1$ and $R^2$ together represent $-A^3-NR^7-A^4-$ in which each of $A^3$ and $A^4$ independently represents $(CH_2)_r$ or $(CH_2CH_2O)_sCH_2CH_2$ in which r is an integer of from 2 to 6, s is 1, 2 or 3, and $R^7$ represents a hydrogen atom or a (1–4C)alkyl group; or (iii) $R^1$ and $R^2$ together with the nitrogen atom to which they are attached represent a piperidinyl group, which piperidinyl group bears a substituent of formula $-A^5-R^8$ at the 4 position, in which $A^5$ represents (1–4C)alkylene and $R^8$ represents piperidin-4-yl.

Preferably (i) $R^1$ represents a methyl group; and $R^2$ represents a group of formula $-A^1-NR^5R^6$ in which $R^5$ represents a hydrogen atom, $R^6$ represents a methyl group and $A^1$ represents $(CH_2)_m$, $(CH_2)_n$-$A^2$-$(CH_2)_p$ or $(CH_2CH_2O)_qCH_2CH_2$ in which m is an integer of from 2 to 10, each of n and p is 1 or 2, $A^2$ is CH=CH, phenyl-1,3-ene, phenyl-1,4-ene, biphenyl-2,2'-ene, cyclohex-1,3-ylene or piperazin-1,4-ylene and q is 1, 2 or 3;

(ii) $R^1$ and $R^2$ together represent -$A^3$-$NR^7$-$A^4$- in which each of $A^3$ and $A^4$ independently represents $(CH_2)_r$ or $(CH_2CH_2O)_sCH_2CH_2$ in which r is an integer of from 2 to 6, s is 1 or 2, and $R^7$ represents a hydrogen atom or a (1–4C)alkyl group; or (iii) $R^1$ and $R^2$ together with the nitrogen atom to which they are attached represent a piperidinyl group, which piperidinyl group bears a substituent of formula -$A^5$-$R^8$ at the 4 position, in which $A^5$ represents propylene and $R^8$ represents piperidin-4-yl.

More preferably, (i) $R^1$ represents a methyl group; and $R^2$ represents a group of formula -$A^1$-$NR^5R^6$ in which $R^5$ represents a hydrogen atom, $R^6$ represents a methyl group and $A^1$ represents $(CH_2)_m$, in which m is 2, 3, 4, 5, 6, 7, 8, 9 or 10; $(CH_2)_n$-$A^2$-$(CH_2)_p$ in which n and p are each 1 and $A^2$ is CH=CH, phenyl-1,3-ene, phenyl-1,4-ene, biphenyl-2,2'-ene or cyclohex-1,3-ylene; $(CH_2)_n$-$A^2$-$(CH_2)_p$ in which n and p are each 2 and $A^2$ is piperazin-1,4-ylene; or $(CH_2CH_2O)_qCH_2CH_2$ in which q is 2 or 3;

(ii) $R^1$ and $R^2$ together represent —$(CH_2)_2$—NH—$(CH_2)_2$—, —$(CH_2)_2$—N($CH_3$)—$(CH_2)_2$—, —$(CH_2)_2$—N($CH_2CH_3$)—$(CH_2)_2$—, —$(CH_2)_2$—NH—$(CH_2)_3$—, or —$(CH_2CH_2O)_2CH_2CH_2$—NH—$(CH_2CH_2O)CH_2CH_2$—; or (iii) $R^1$ and R together with the nitrogen atom to which they are attached represent a piperidinyl group, which piperidinyl group bears a substituent of formula -$A^5$-$R^8$ at the 4 position, in which $A^5$ represents propylene and $R^8$ represents piperidin-4-yl.

A particularly preferred sub-group of compounds is that in which $R^1$ represents a methyl group and $R^2$ represents a group of formula -$A^1$-$NR^5R^6$ in which $R^5$ represents a hydrogen atom, $R^6$ represents a methyl group and $A^1$ represents $(CH_2)_m$ or $CH_2$—CH=CH—$CH_2$, in which m is an integer of from 2 to 6.

Compounds belonging to this sub-group have been found to exhibit particularly good potency as inhibitors of one or more of the above receptor tyrosine kinases.

Within this sub-group, preferably $A^1$ represents $(CH_2)_m$ or $CH_2$—CH=CH—$CH_2$, in which m is 2, 3 or 4.

More preferably $A^1$ represents $(CH_2)_2$,$(CH_2)_3$ or $CH_2$—CH=CH—$CH_2$.

Especially preferred are compounds in which $A^1$ represents$(CH_2)_2$.

Another preferred sub-group of compounds is that in which $R^1$ and $R^2$ together represent -$A^3$-$NR^7$-$A^4$- in which each of $A^3$ and $A^4$ independently represents$(CH_2)_r$ or $(CH_2CH_2O)_sCH_2CH_2$ in which r is an integer of from 2 to 6, and s is 1, 2 or 3, and $R^7$ represents a hydrogen atom or a (1–4C)alkyl group.

Compounds belonging to this sub-group have also been found to exhibit particularly good potency.

In this sub-group, preferably $R^1$ and $R^2$ together represent —$(CH_2)_2$—$NR^7$—$(CH_2)_2$— or —$(CH_2)_2$—$NR^7$—$(CH_2)_3$—, especially —$(CH_2)_2$—$NR^7$—$(CH_2)_2$—.

Examples of particular values for $R^7$ are hydrogen, methyl, ethyl, propyl, prop-2-yl and butyl.

Compounds in which $R^7$ represents hydrogen are especially preferred.

Referring to $R^3$ and $R^4$, examples of particular values are: hydrogen;

for a halogen atom: fluorine, chlorine or bromine, especially bromine;

for a (1–4C)alkyl group: methyl;

for a (1–4C)alkoxy group: methoxy;

for an unsubstituted or substituted phenyl group: phenyl;

for $R^8$, $R^{10}$, $R^{12}$ and $R^{14}$: methyl or phenyl;

for $R^9$, $R^{11}$, $R^{13}$ and $R^{15}$: hydrogen; and for a group of formula $R^{12}C(O)N(R^{13})$—: $CH_3C(O)NH$— and $C_6H_5C(O)NH$—.

Preferably $R^3$ and $R^4$ each independently represents a hydrogen atom, a bromine atom, $CH_3C(O)NH$—, or $C_6H_5C(O)NH$—. More preferably $R^3$ and $R^4$ each independently represents a hydrogen atom.

Another preferred group of compounds of formula (I) are compounds in which:

(i) $R^1$ represents a methyl group and $R^2$ represents a group of formula -$A^1$-$NHCH_3$ in which $A^1$ represents $(CH_2)_m$, $CH_2CH$=$CHCH_2$, $CH_2$-phenylene-$CH_2$, or $CH_2$-cyclohexylene-$CH_2$, in which m is an integer of from 2 to 8; or (ii) $R^1$ and $R^2$ together represent —$(CH_2)_2$—NH—$(CH_2)_2$—, —$(CH_2)_2$—N($CH_3$)—$(CH_2)_2$—, —$(CH_2)_2$—N($CH_2CH_3$)—$(CH_2)_2$— or —$(CH_2)_2$—NH—$(CH_2)_3$—; and $R^3$ and $R^4$ are each independently hydrogen.

Compounds of the above sub-group have been found to exhibit particularly good potency as inhibitors of one or more receptor tyrosine kinases. In particular, such compounds have demonstrated $IC_{50}$ values for inhibition of the VEGFR tyrosine kinase of less than 1 µM in the intracellular $Ca^{2+}$ FLIPR or immunoprecipitation assay described below.

A more preferred sub-group of compounds within the above sub-group are compounds in which:

(i) $R^1$ represents a methyl group and $R^2$ represents a group of formula -$A^1$-$NHCH_3$ in which $A^1$ represents $(CH_2)_m$, $CH_2CH$=$CHCH_2$, or $CH_2$—(1,4-phenylene)-$CH_2$ in which m is 2 or 3; or (ii) $R^1$ and $R^2$ together represent —$(CH_2)_2$—NH—$(CH_2)_2$—, —$(CH_2)_2$—N($CH_3$)—$(CH_2)_2$— —$(CH_2)_2$—N($CH_2CH_3$)—$(CH_2)_2$— or —$(CH_2)_2$—NH—$(CH_2)_3$—.

Compounds belonging to this more preferred sub-group of compounds have demonstrated $IC_{50}$ values for inhibition of both the VEGFR and PDGFR tyrosine kinases of less than 1 µM in the intracellular $Ca^{2+}$ FLIPR or immunoprecipitation assay described below.

A particularly preferred sub-group of compounds of formula (I) are compounds of formula (Ia):

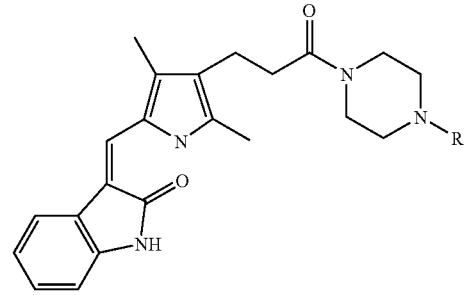

(Ia)

wherein R is hydrogen, methyl, or ethyl, and pharmaceutically-acceptable salts thereof.

Compounds of formula (Ia) that may be given special mention are:

3-[3,5-dimethyl-4-(3-oxo-3-piperazin-1-ylpropyl)-1H-pyrrol-2-ylmethylene]-1,3-dihydroindol-2-one and 3-[3,5-dimethyl-4-[3-oxo-3-(4-ethyl)piperazin-1-ylpropyl]-1H-pyrrol-2-ylmethylene]-1,3-dihydroindol-2-one.

Especially preferred is the compound 3-[3,5-dimethyl-4-(3-oxo-3-piperazin-1-ylpropyl)-1H-pyrrol-2-ylmethylene]-1,3-dihydroindol-2-one, and pharmaceutically-acceptable salts thereof. This compound has been found to be a highly potent and selective inhibitor of PDGFR, c-Kit, VEGFR and Flt-3. It has also been found to have high solubility in water and to possess excellent absorption when administered orally to rats.

Another compound of formula (I) that may be given special mention is 3-[3,5-dimethyl-4-(3-oxo-3-homopiperazin-1-ylpropyl)-1H-pyrrol-2-ylmethylene]-1,3-dihydroindol-2-one.

The compounds of formula (I) are useful as receptor tyrosine kinase inhibitors for the treatment of proliferative disorders, such as forms of cancer which include, but are not limited to acute myeloid leukemia, small cell lung cancer, prostate cancer, gastrointestinal cancer, breast cancer and brain cancer, and other proliferative disorders, such as restenosis. The compounds may also be useful in restricting the growth of solid tumors.

According to another aspect, the present invention provides a process for the preparation of a compound of formula (I), which comprises (a) reacting a compound of formula (II)

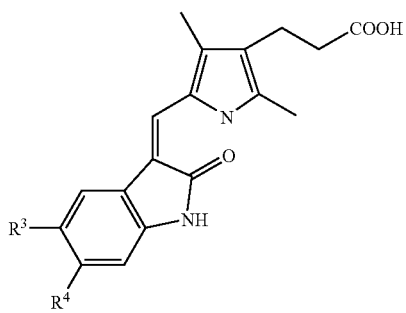

or a reactive derivative thereof, with a compound of formula (III)

 (III)

or a salt thereof, in which $R^1$, $R^2$, $R^3$ and $R^4$ are as defined hereinabove, or (b) for a compound of formula (I) in which $R^5$ or $R^7$ represents a hydrogen atom, deprotecting a compound of formula (IV)

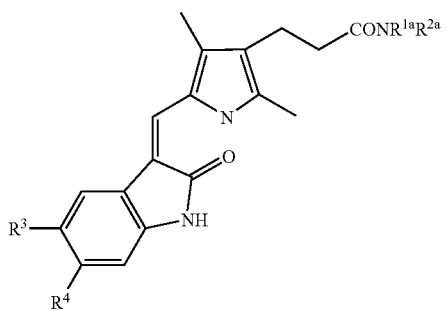

in which $R^{1a}$ and $R^{2a}$ are as defined hereinabove for $R^1$ and $R^2$, except in that $R^5$ or $R^7$ is replaced with a group $R^{5a}$ or $R^{7a}$ respectively, in which $R^{5a}$ and $R^{7a}$ each represents an amine protecting group, and $R^3$ and $R^4$ are as defined hereinabove;

followed, if a pharmaceutically-acceptable salt is required, by forming a pharmaceutically-acceptable salt.

In process (a), the reaction of a compound of formula (II) with a compound of formula (III) may conveniently be performed using a conventional amide coupling method. For example, an acid of formula (II) may be treated with a coupling agent, such as benzotriazol-1-yl-oxy-trispyrrolidinophosphonium hexafluorophosphate (PyBOP) or o-(7-azabenzotriazol-1-yl)-N,N,N'N'-tetramethyluronium hexafluorophosphate (HATU), in the presence of a base, such as N,N-diisopropylethylamine, and 1-hydroxy-7-azabenzotriazole (HOAt), followed by addition of the compound of formula (III). Convenient solvents include polar aprotic organic solvents, such as dimethylformamide. The temperature is conveniently in the range of from 0 to 50° C. Alternatively, the compound of formula (II) may be converted into an acid halide, such as the chloride, and then reacted with the compound of formula (III).

In process (b), the amine protecting group presented by $R^{5a}$ or $R^{7a}$ may be a conventional amine protecting group. Examples of amine protecting groups are described in Greene and Wuts, *Protecting Groups in Organic Synthesis*, 2nd Edition, John Wiley & Sons, NY, 1991 and McOmie, *Protecting Groups in Organic Chemistry*, Plenum Press, NY, 1973. Examples of amine protecting groups include acyl groups, for example (1–6C)alkanoyl groups, such as acetyl; (1–6C)alkoxycarbonyl groups, such as t-butoxycarbonyl; and arylmethoxycarbonyl groups, such as benzyloxycarbonyl; and arylmethyl groups, such as benzyl.

An acyl amine protecting group may conveniently be removed by treatment with an acid, such as trifluoroacetic acid.

Compounds of formula (IV) may be prepared by reacting a compound of formula (II) with an amine of formula (V)

 (V)

in which $R^{1a}$ and $R^{2a}$ are as defined hereinabove, following the method of process step (a).

Compounds of formula (II) are known, for example from WO 99/61422. They may also be prepared by reacting a compound of formula (VI)

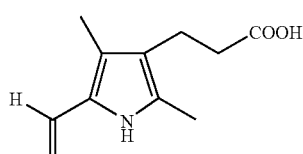

with a compound of formula (VII)

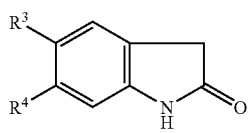

The reaction is conveniently performed in the presence of a base, such as piperidine, in an organic solvent, such as ethanol, and under reflux.

Compounds of formula (VII) are known, for example from WO 99/61422.

Compounds of formula (VI) may be prepared by reacting a compound of formula (VIII)

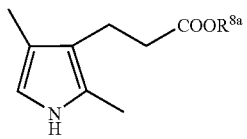

(VIII)

in which $R^{8a}$ represents a carboxyl protecting group, for example a (1–6C)alkyl group such as methyl, with phosphorus oxychloride and dimethylformamide, followed by removal of the protecting group $R^{8a}$, for example by alkali hydrolysis.

Compounds of formula (VIII) may be prepared via the corresponding carboxylic acid ($R^{8a}$ is hydrogen) following methods as described in the accompanying examples.

Certain of the intermediates described herein are believed to be novel, for example the compounds of formula (IV). All such novel intermediates are provided as further aspects of the invention.

Pharmaceutical Compositions

When used as pharmaceuticals, the compounds of the invention will usually be administered in a pharmaceutical composition. The compositions comprise a compound of the invention as the active ingredient, together with a pharmaceutically-acceptable diluent or carrier. The compositions may be formulated for any route of administration, in particular for oral, rectal, transdermal, subcutaneous, intravenous, intramuscular or intranasal administration. The compositions may be formulated in any conventional form, for example, as tablets, capsules, solutions, suspensions, dispersions, syrups, sprays, gels, suppositories, patches and emulsions.

The preparation of a suitable pharmaceutical composition for a particular mode of administration is well within the scope of those skilled in the pharmaceutical arts. Additionally, the ingredients for such compositions are commercially available from, for example, Sigma (St. Louis, Mo.). By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

According to another aspect, the present invention provides a pharmaceutical composition, which comprises a therapeutically-effective amount of a compound of formula (I) or a pharmaceutically-acceptable salt thereof, together with a pharmaceutically-acceptable diluent or carrier.

In a preferred embodiment, the pharmaceutical compositions of the invention are suitable for oral administration. Suitable pharmaceutical compositions for oral administration may be in the form of capsules, tablet, pills, lozenges, cachets, dragees, powders, granules, or as a solution or suspension in a liquid, and the like; each containing a predetermined amount of a compound of the present invention as an active ingredient. A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. In addition, the active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, can be prepared and filled into a soft gelatin capsule.

In another preferred embodiment, the compound of the invention can be formulated for injection, for example for intravenous injection. A typical composition for intravenous injection consists of a sterile isotonic aqueous solution containing, for example, active compound and dextrose or sodium chloride, or a mixture of dextrose and sodium chloride. Other examples of suitable excipients include lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetraacetic acid; a stabilizing agent, for example, a cyclodextrin; and an anti-oxidant, for example, sodium metabisulphite, may be included in the formulation.

According to another aspect, the present invention provides a compound of formula (I) or a pharmaceutically-acceptable salt thereof for use in therapy.

The compounds of formula (I) are useful as receptor tyrosine kinase inhibitors. According to another aspect, therefore, the present invention provides the use of a compound of formula (I) or a pharmaceutically-acceptable salt thereof, for the manufacture of a medicament for the treatment of a condition responsive to a tyrosine kinase inhibitor.

According to yet another aspect, the present invention provides a pharmaceutical composition for use in the treatment of a condition responsive to a tyrosine kinase inhibitor, which comprises a compound of formula (I) or a pharmaceutically-acceptable salt thereof.

The present invention also provides a method of treating a condition responsive to a tyrosine kinase inhibitor, which comprises administering to a patient in need of treatment an effective amount of a compound of formula (I) or a pharmaceutically-acceptable salt thereof.

The patient may be, for example, a mammal, such as a companion animal, and is preferably a human.

The dose (or effective amount) of the compound administered to a patient will depend upon many factors, including the particular compound used, the nature and severity of the condition being treated, the species of the patient, the weight of the patient and the route of administration. In general, a dose in the range of from 0.01 to 100 μM/kg of bodyweight will be administered.

The following non-limiting examples illustrate representative pharmaceutical compositions of the invention.

FORMULATION EXAMPLE A

Hard gelatin capsules for oral administration are prepared as follows:

| Ingredients | Amount |
| --- | --- |
| Compound of the invention | 250 mg |
| Lactose (spray-dried) | 200 mg |
| Magnesium stearate | 10 mg |

Representative Procedure:
The ingredients are thoroughly blended and then loaded into a hard gelatine capsule (460 mg of composition per capsule)

FORMULATION EXAMPLE B

Hard gelatin capsules for oral administration are prepared as follows:

| Ingredients | Amount |
| --- | --- |
| Compound of the invention | 20 mg |
| Starch | 89 mg |
| Microcrystalline cellulose | 89 mg |
| Magnesium stearate | 10 mg |

Representative Procedure:
The ingredients are thoroughly blended and then passed through a No. 45 mesh U.S. sieve and loaded into a hard gelatine capsule (200 mg of composition per capsule)

FORMULATION EXAMPLE C

Capsules for oral administration are prepared as follows:

| Ingredients | Amount |
| --- | --- |
| Compound of the invention | 100 mg |
| Polyoxyethylene sorbitan monooleate | 50 mg |
| Starch powder | 250 mg |

Representative Procedure:
The ingredients are thoroughly blended and then loaded into a hard gelatine capsule (300 mg of composition per capsule)

FORMULATION EXAMPLE D

Tablets for oral administration are prepared as follows:

| Ingredients | Amount |
| --- | --- |
| Compound of the invention | 250 mg |
| Microcrystalline cellulose | 400 mg |
| Silicon dioxide fumed | 10 mg |
| Stearic acid | 5 mg |

Representative Procedure:
The ingredients are thoroughly blended and then loaded into a hard gelatine capsule (460 mg of composition per capsule)

FORMULATION EXAMPLE E

An injectable formulation is prepared as follows:

| Ingredients | Amount |
| --- | --- |
| Compound of the invention | 0.2 g |
| Sodium acetate buffer solution (0.4 M) | 400 mg |
| HCl (0.5 N) or NaOH (0.5 N) | q.s. to pH 4 |
| Water (distilled, sterile) | q.s. to 20 mL |

Representative Procedure:
The above ingredients are blended and the pH is adjusted to 4±0.5 using 0.5 N HCl or 0.5 N NaOH.

SYNTHETIC EXAMPLES

The following synthetic examples are offered to illustrate the invention, and are not to be construed in any way as limiting the scope of the invention.

General
Reagents and solvents were used as received from commercial suppliers unless otherwise noted. All reactions were carried out at room temperature and without rigorous exclusion of ambient atmosphere unless otherwise noted. Ion-spray mass spectra (IS-MS) were obtained using a PE Sciex API 150EX mass spectrometer. Nuclear magnetic resonance (NMR) spectra were recorded at 300 MHz. Chemical shifts (δ) are reported in parts per million downfield of tetramethylsilane. Analytical reversed-phase HPLC (RP-HPLC) was performed on an HP1100 instrument using a 2.1 mm×50 mm, 3.5 μm $C_{18}$ Zorbax Plus Bonus-RP column. For the analytical separations, a 0.5 minute isocratic period was followed by a 4.5 minute gradient of 0.1% trifluoroacetic acid/acetonitrile (ACN) in 0.1% water at a flow rate of 0.5 mL/minute, Preparative RP-HPLC was performed using trifluoroacetic acid (TFA) buffered ACN/water gradients on a Varian ProStar system using 2.5- or 10 cm×25 cm, 8 μm $C_{18}$ Rainin Dynamax columns and flow rates of 10- or 50 mL/minute, respectively.

Preparetion of Intermediates

Intermediate 1

2-Carboxyethyl-3,5-dimethyl-1H-pyrrole-4-carboxylic acid 3,5-Dimethyl-2,4-pyrrole dicarboxylic acid, diethyl ester (200 g, 836 mmol) was placed in a 1 L beaker and treated with 400 mL concentrated sulfuric acid ($H_2SO_4$). The mixture was stirred, heated to 45 C with the aid of a heat gun and then maintained at 36–42 C for 25 minutes. The reaction mixture was poured into 3 L crushed ice and stirred for 30 minutes. The yellow solid was recovered by filtration and washed with 200 mL water. The solid was transferred to a 4 L Erlenmeyer flask and treated with 2 L 1 N sodium hydroxide solution (NaOH) followed by 100 mL 10 N NaOH. The basic mixture was filtered and the yellow solid residue was discarded. The filtrate was acidified with $H_2SO_4$. The resulting solid was recovered by suction filtration and washed with 2×500 mL water. After suction drying, the material was transferred to a 6 L Erlenmeyer flask and digested briefly in 4 L acetone. After standing overnight at room temperature (RT), the solid was collected by filtration and dried in a vacuum dessicator to afford 139 g, 659 mmol, 79% of the title compound. $^1$H NMR (DMSO-d$_6$) δ 4.22 (q, 2H), 2.44 (s, 3H), 2.38 (s, 3H), 1.27 (t, 3H).

Intermediate 2

2-Carboxyethyl-3,5-dimethyl-1H-pyrrole

Intermediate 1 (137 g, 650 mmol) was placed in a 500 mL Erlenmeyer flask and treated with ethanolamine (80 g, 1.3 mol). The mixture was then heated to 220 C in a heating mantle, producing a brown solution over approximately 30 minutes, at which time gas evolution had essentially ceased. The reaction was heated for 30 minutes more, then poured into 2 L ice water. The crude product was collected by suction filtration and then digested in 700 mL 95% ethanol (EtOH). The mixture was filtered while hot and the filtrate was slowly cooled to RT and then to −20 C. The resulting crystals were collected by suction filtration and dried in a vacuum dessicator to afford 75.6 g, 453 mmol, 70% of the title compound. $^1$H NMR (DMSO-d$_6$) δ 5.72 (s, 1H), 4.17 (q, 2H), 2.18 (s, 3H), 2.13 (s, 3H), 1.25 (t, 3H).

Intermediate 3

2-Carboxyethyl-3,5-dimethyl-1H-pyrrole-4-carboxaldehyde

Intermediate 2 (75.6 g, 453 mmol) was placed in a dry 1 L, 3-necked round-bottom flask. The solid was treated with anhydrous N N-dimethylformamide (DMF, 43.8 mL, 566 mmol). The flask was shaken to distribute the DMF throughout the solid. The flask was cooled in an ice bath and to the mixture was added phosphorous oxychloride (POCl$_3$, 52.7 mL, 566 mmol) over 30 minutes via an addition funnel. The flask was shaken to evenly distribute the reagents. The flask was then immersed in a 100 C oil bath and heated with magnetic stirring for 6 hours. The resulting deep red mixture was cooled in an ice water bath and treated with 200 mL ice water, resulting in a vigorous, exothermic reaction. After addition of 200 mL additional ice water, the mixture was adjusted to pH 5 with a saturated solution of sodium acetate (NaOAc). The crude product was isolated by suction filtration and recrystallized from 700 mL hot 1:1 EtOH:water to afford 65.8 g, 337 mmol, 74% of the title compound as dark needles. $^1$H NMR (DMSO-d$_6$) δ 9.88 (s, 1H), 4.23 (q, 2H), 2.46 (s, 3H), 2.43 (s, 3H), 1.28 (t, 3H).

Intermediate 4

3-(5-Carboxyethyl-2,4-dimethyl-1H-pyrrol-3-yl) propenoic acid

Intermediate 3 (65.8 g, 337 mmol) and malonic acid (39.0 g, 375 mmol) were combined in a 500 mL, 1-necked round bottom flask, treated with 350 mL absolute EtOH, and brought to reflux for 30 minutes. To the resulting dark solution was added aniline (34.0 mL, 375 mmol) and the mixture was refluxed for an additional 5 hours. Solvent was removed under reduced pressure and the residue was treated with 400 mL 2.5 M hydrochloric acid (HCl), warmed, and then allowed to cool to RT. A purple solid was collected by suction filtration, transferred to a 1 L beaker and treated with 250 mL 2 N NaOH with stirring. The resulting slurry was filtered and the solids were washed with 100 mL dilute base. The purple residue was discarded. The red filtrate was cooled in an ice bath, stirred and acidified with approximately 70 mL 6 M HCl. The resulting thick, white paste was collected by suction filtration, washed with water, and dried in air to afford the title compound. $^1$H NMR (DMSO-d$_6$) δ 7.52 (d, 1H), 5.93 (d, 1H), 4.22 (q, 2H), 2.35 (s, 3H), 2.31 (s, 3H), 1.28 (t, 3H).

Intermediate 5

3-(2-Carboxyethyl-2,4-dimethyl-1H-pyrrol-3-yl) propionic acid

Intermediate 4 was dissolved in 220 mL 2 N NaOH and combined with 3.5 g 10% palladium on activated carbon. The mixture was hydrogenated at 50 psi for 28 hours, then suction filtered over Celite. The Celite was washed with 50 mL water. An aliquot of the filtrate was evaporated to dryness and complete reduction to the title compound was confirmed by $^1$H NMR (D$_2$O) δ 4.07 (q, 2H), 2.46 (t, 2H), 2.06 (s, 3H), 2.05 (t, 2H), 2.00 (s, 3H), 1.13 (t, 3H). The remaining filtrate was carried forward to the next step without further manipulation.

Intermediate 6

3-(2,4-Dimethyl-1H-pyrrol-3-yl)propionic acid

The filtrate from the previous step containing Intermediate 6 was treated with 30 mL 10 N NaOH and heated at reflux for 20 hours. An aliquot of the reaction mixture was acidified and evaporated to dryness. Complete hydrolysis/decarboxylation to the title compound was confirmed by $^1$H NMR (DMSO-d$_6$) δ 9.86 (s, 1H), 6.18 (2, 2H), 2.42 (m, 2H), 2.03 (s, 3H), 1.93 (m, 2H), 1.87 (s, 3H). The reaction mixture was carried forward to the next step without further manipulation.

Intermediate 7

Methyl 3-(2,4-dimethyl-1H-pyrrol-3-yl)propionate

The solution of Intermediate 6 from the previous step was concentrated at 60 C under reduced pressure to approximately 200 mL, cooled in an ice water bath and acidified to pH 2 using approximately 50 ml 50% H$_2$SO$_4$. The resulting mixture was filtered through a glass frit. The filtrate was extracted with 2×100 mL diethyl ether (Et$_2$O) and the residue was extracted with 3×100 mL Et$_2$O. The combined red organic extracts were washed with 2×100 mL water, transferred to a 2 L Erlenmeyer flask, and treated with stirring with 680 mL of an ethereal solution of diazomethane. After stirring 30 minutes at RT, excess diazomethane was quenched with glacial acetic acid (HOAc). The reaction mixture was extracted with 2×200 mL saturated aqueous sodium bicarbonate (NaHCO$_3$), dried over anhydrous magnesium sulfate (MgSO$_4$), filtered, and evaporated to afford 52.6 g of crude red oil. This was purifed by bulb-to-bulb distillation at 145 C and 0.2 mm Hg pressure to afford the title compound (38.4 g, 211 mmol, 63% overall from Intermediate 3). $^1$H NMR (DMSO-d$_6$) δ 9.92 (s, 1H), 6.22 (s, 1H), 3.54 (s, 3H), 2.52 (t, 2H), 2.32 (t, 3H), 2.02 (s, 3H), 1.87 (s, 3H).

Intermediate 8

3-(5-Formyl-2,4-dimethyl-1H-pyrrol-3-yl)propionic acid

To a dry 250 mL 3-necked, round-bottom flask was added anhydrous DMF (13.8 g mL, 189 mmol). This was cooled in an ice water bath and treated with $POCl_3$ (15.0 mL, 160 mmol) dropwise over 10 minutes. The mixture was diluted with 120 mL anhydrous 1,2-dichloroethane (DCE) and warmed to RT, producing a pale orange solution. The mixture was cooled to −10 C in an ice brine bath, at which point a precipitate formed. Intermediate 7 (14.5 g, 80.0 mmol) dissolved in 30 mL DCE was added dropwise over 10 minutes. The reaction mixture was removed from the cooling bath, stirred at RT for 10 minutes and then evaporated under reduced pressure at 30 C. The residue was transferred to a 2 L beaker using approximately 100 mL methanol (MeOH), treated with 800 mL 2 N NaOH, heated to 90 C and then allowed to cool to RT. The orange solution was extracted with 2×200 mL $Et_2O$, heated to 50 C, treated with activated charcoal, cooled to RT, and filtered through a pad of Celite. The filtrate was cooled in an ice water bath and acidified to pH 3 using approximately 120 mL 6 N HCl. The resulting solid was collected by suction filtration, washed with 3×40 mL water, and dried in air to afford 11.2 g, 57.0 mmol, 72% of the title compound as a brownish powder. $^1$H NMR (DMSO-$d_6$) δ 9.40 (s, 1H), 2.52 (t, 2H), 2.29 (t, 2H), 2.19 (s, 3H), 2.14 (s, 3H).

Intermediate 9

3-[2,4-Dimethyl-5-(2-oxo-1,2-dihydroindol-3-ylidenemethyl)-1H-pyrrol-3-yl]propionic acid Intermediate 8 (11 g, 57 mmol) and oxindole (7.6 g, 57 mmol) were combined in a 200 mL round-bottom flask, slurried in 150 mL EtOH, treated with piperidine (8.5 mL, 86 mmol), and heated to reflux for 4 hours. The reaction mixture was cooled to RT, treated with HOAc (14.4 mL, 250 mmol), returned briefly to reflux, cooled again and filtered. The orange solid was collected by suction filtration, washed with 100 mL hot 1:1 HOAc:EtOH followed by 100 mL hot EtOH, and dried in air to afford 15 g, 50 mmol, 87% of the title compound. $^1$H NMR (DMSO-$d_6$) δ 10.8 (s, 1H), 7.71 (d, 1H), 7.55 (s, 1H), 7.07 (t, 1H), 6.95 (t, 1H), 6.96 (d, 1H), 2.63 (t, 2H), 2.33 (t, 2H), 2.28 (s, 3H), 2.25 (s, 3H).

Intermediate 10

4-{3-[2,4-Dimethyl-5-(2-oxo-1,2-dihydroindol-3-ylidenemethyl)-1H-pyrrol-3-yl]-propionyl}-piperazine-1-carboxylic acid tert-butyl ester Intermediate 9 (6.2 g, 20 mmol), mono-Boc piperazine (4.1 g, 22 mmol), and 1-hydroxy-7-azabenzotriazole (HOAT, 3.0 g, 22 mmol) were dissolved in 50 mL anhydrous DMF and treated with N,N-diisopropylethylamine (DIEA, 3.5 mL, 20 mmol) followed by benzotriazol-1-yl-oxy-trispyrrolidino-phosphonium hexafluorophosphate (PyBOP, 11.4 g, 22 mmol). The resulting mixture was stirred overnight at RT, depositing a yellow solid. The solid was collected by suction filtration, washed with DMF and ACN and dried to afford 1.3 g of Intermediate 10. The filtrate was evaporated and fractionated by chromatography on 700 cc of silica gel using 5% MeOH in dichloromethane (DCM) eluent. Product-containing fractions were combined and evaporated, then digested in 100 mL ACN. After cooling to RT, the fine yellow solid was collected by suction filtration, washed with 2×20 mL ACN, and dried to afford an additional 5.7 g of the title compound. In all, 7.0 g, 15 mmol, 75% of product was obtained. $^1$H NMR (DMSO-$d_6$) δ 10.7 (s, 1H), 7.70 (d, 1H), 7.55 (s, 1H), 7.07 (t, 1H), 6.95 (t, 1H), 6.84 (d, 1H), 3.41–3.19 (m, 8H), 2.62 (t, 2H), 2.43 (t, 2H), 2.28 (s, 3H), 2.24 (s, 3H), 1.35 (s, 9H). IS-MS, calcd. m/z for $C_{27}H_{34}N_4O_4$ [M]$^+$: 478; obsd. 478.2.

Example 1

3-[3,5-dimethyl-4-(3-oxo-3-piperazin-1-yl-propyl)-1H-pyrrol-2-ylmethylene]-1,3-dihydroindol-2-one, trifluoroacetate Intermediate 10 (4.78 g, 10.0 mmol) was slurried in 20 mL DCM and treated at room temperature with 20 mL TFA. After 30 minutes the reaction mixture was evaporated under reduced pressure, then dissolved in 20 mL chloroform and re-evaporated two times. The residue was re-dissolved in 20 mL chloroform and added dropwise to 200 mL $Et_2O$. The resulting yellow solid was collected by suction filtration, washed with 3×20 mL $Et_2O$, and dried to afford 4.8 g, 9.7 mmol, 97% of the title compound. $^1$H NMR (DMSO-$d_6$) δ 10.8 (s, 1H), 8.74 (br s, 2H), 7.71 (d, 1H), 7.56 (s, 1H), 7.07 (t, 1H), 6.96 (t, 1H), 6.85 (d, 1H), 3.62 (br s, 4H), 3.02 (br s, 4H), 2.62 (t, 2H), 2.5 (t, 2H), 2.28 (s, 3H), 2.25 (s, 3H). IS-MS, calcd. m/z for $C_{22}H_{26}N_4O_2$ [M+H$^+$]$^+$: 379.2; obsd. 379.0.

Example 1a (Alternative Preparation)

3-[3,5-dimethyl-4-(3-oxo-3-piperazin-1-yl-propyl)-1H-pyrrol-2-ylmethylene]-1,3-dihydroindol-2-one, trifluoroacetate Intermediate 9 (0.31 g, 1.0 mmol) was dissolved in 3 mL anhydrous DMF and treated with HOAT (0.14 g, 1.0 mmol) followed by O-(7-azabenzotriazol-1-yl)-N,N,N',N'-tetramethyluronium hexafluorophosphate (HATU, 0.38 g, 1.0 mmol). After stirring 10 minutes at RT, the reaction mixture was added to a solution of piperazine (0.17 g, 2.0 mmol) and stirred for two days. The reaction mixture was then fractionated by preparative reversed-phase HPLC. The appropriate fractions were combined and lyophilized to afford 0.16 g, 0.34 mmol, 34% of the title compound.

Example 2

3-[2,4-dimethyl-5-(2-oxo-1,2-dihydro-indol-3-ylidenemethyl)-1H-pyrrol-3-yl]-N-methyl-N-(2-methylaminoethyl)-propionamide, trifluoroacetate Intermediate 10 (0.062 g, 0.20 mmol) was dissolved in 0.67 mL anhydrous DMF and treated with HOAT (0.030 g, 0.22 mmol) and HATU (0.084 g, 0.22 mmol). After stirring at RT for 15 minutes, the activated acid was added to a vial containing a solution of N,N'-dimethylethylenediamine (0.043 mL, 0.40 mmol) in 0.50 mL anhydrous DMF. The reaction mixture was agitated overnight on an orbiting shaker, then diluted with 0.50 mL of 30% aqueous TFA, filtered, and fractionated by preparative reversed-phase HPLC. The appropriate fractions were combined and lyophilized to afford 0.005 g, 0.010 mmol, 5% of the title compound. IS-MS, calcd. m/z for $C_{22}H_{28}N_4O_2$ [M+H$^+$]$^+$: 381.2; obsd. 381.0.

Examples 3 to 24

In a manner similar to that described in Example 1a and 2, coupling of Intermediate 10 with other amines afforded the compounds of Examples 3 to 24.

Example 3

3-[2,4-dimethyl-5-(2-oxo-1,2-dihydro-indol-3-ylidenemethyl)-1H-pyrrol-3-yl]-N-methyl-N-(3-methylaminopropyl)-propionamide, trifluoroacetate IS-MS, calcd. m/z for $C_{23}H_{30}N_4O_2$ $[M+H^+]^+$: 395.2; obsd. 395.0.

Example 4

3-[2,4-dimethyl-5-(2-oxo-1,2-dihydro-indol-3-ylidenemethyl)-1H-pyrrol-3-yl]-N-methyl-N-(4-methylaminobutyl)-propionamide, trifluoroacetate IS-MS, calcd. m/z for $C_{24}H_{32}N_4O_2$ $[M+H^+]^+$: 409.3; obsd. 409.0.

Example 5

3-[2,4-dimethyl-5-(2-oxo-1,2-dihydro-indol-3-ylidenemethyl)-1H-pyrrol-3-yl]-N-methyl-N-(5-methylaminopentyl)-propionamide, trifluoroacetate IS-MS, calcd. m/z for $C_{25}H_{34}N_4O_2$ $[M+H^+]^+$: 423.3; obsd. 423.2.

Example 6

3-[2,4-dimethyl-5-(2-oxo-1,2-dihydro-indol-3-ylidenemethyl)-1H-pyrrol-3-yl]-N-methyl-N-(6-methylaminohexyl)-propionamide, trifluoroacetate IS-MS, calcd. m/z for $C_{26}H_{36}N_4O_2$ $[M+H^+]^+$: 437.3; obsd. 437.2.

Example 7

3-[2,4-dimethyl-5-(2-oxo-1,2-dihydro-indol-3-ylidenemethyl)-1H-pyrrol-3-yl]-N-methyl-N-(7-methylaminoheptyl)-propionamide, trifluoroacetate IS-MS, calcd. m/z for $C_{27}H_{38}N_4O_2$ $[M+H^+]^+$: 451.3; obsd. 451.2.

Example 8

3-[2,4-dimethyl-5-(2-oxo-1,2-dihydro-indol-3-ylidenemethyl)-1H-pyrrol-3-yl]-N-methyl-N-(8-methylaminooctyl)-propionamide, trifluoroacetate IS-MS, calcd. m/z for $C_{28}H_{40}N_4O_2$ $[M+H^+]^+$: 465.3; obsd. 465.2.

Example 9

3-[2,4-dimethyl-5-(2-oxo-1,2-dihydro-indol-3-ylidenemethyl)-1H-pyrrol-3-yl]-N-methyl-N-(9-methylaminononyl)-propionamide, trifluoroacetate IS-MS, calcd. m/z for $C_{29}H_{42}N_4O_2$ $[M+H^+]^+$: 479.3; obsd. 479.2.

Example 10

3-[2,4-dimethyl-5-(2-oxo-1,2-dihydro-indol-3-ylidenemethyl)-1H-pyrrol-3-yl]-N-methyl-N-(10-methylaminodecyl)-propionamide, trifluoroacetate IS-MS, calcd. m/z for $C_{30}H_{44}N_4O_2$ $[M+H^+]^+$: 493.4; obsd. 492.8.

Example 11

3-[2,4-dimethyl-5-(2-oxo-1,2-dihydro-indol-3-ylidenemethyl)-1H-pyrrol-3-yl]-N-methyl-N-(12-methylaminododecyl)-propionamide, trifluoroacetate IS-MS, calcd. m/z for $C_{32}H_{48}N_4O_2$ $[M+H^+]^+$: 521.4; obsd. 520.8.

Example 12

3-[2,4-dimethyl-5-(2-oxo-1,2-dihydro-indol-3-ylidenemethyl)-1H-pyrrol-3-yl]-N-methyl-N-(4-methylaminobut-2-enyl)-propionamide, trifluoroacetate IS-MS, calcd. m/z for $C_{24}H_{30}N_4O_2$ $[M+H^+]^+$: 407.2; obsd. 407.0.

Example 13

3-[2,4-dimethyl-5-(2-oxo-1,2-dihydro-indol-3-ylidenemethyl)-1H-pyrrol-3-yl]-N-methyl-N-(8-methylamino-3,6-dioxaoctyl)-propionamide, trifluoroacetate IS-MS, calcd. m/z for $C_{26}H_{36}N_4O_4$ $[M+H^+]^+$: 469.3; obsd. 469.0.

Example 14

3-[2,4-dimethyl-5-(2-oxo-1,2-dihydro-indol-3-ylidenemethyl)-1H-pyrrol-3-yl]-N-methyl-N-(11-methylamino-3,6,9-trioxaundecyl)propionamide, trifluoroacetate IS-MS, calcd. m/z for $C_{28}H_{40}N_4O_5$ $[M+H^+]^+$: 513.3; obsd. 512.8.

Example 15

3-[2,4-dimethyl-5-(2-oxo-1,2-dihydro-indol-3-ylidenemethyl)-1H-pyrrol-3-yl]-N-methyl-N-(3-methylaminomethylphenyl-methyl)propionamide, trifluoroacetate IS-MS, calcd. m/z for $C_{28}H_{32}N_4O_2$ $[M+H^+]^+$: 457.3; obsd. 457.0.

Example 16

3-[2,4-dimethyl-5-(2-oxo-1,2-dihydro-indol-3-ylidenemethyl)-1H-pyrrol-3-yl]-N-methyl-N-(4-methylaminomethylphenyl-methyl)propionamide, trifluoroacetate IS-MS, calcd. m/z for $C_{28}H_{32}N_4O_2$ [M+H$^+$]$^+$: 457.3; obsd. 457.2.

Example 17

3-[2,4-dimethyl-5-(2-oxo-1,2-dihydro-indol-3-ylidenemethyl)-1H-pyrrol-3-yl]-N-methyl-N-(3-methylaminomethylcyclohexyl-methyl)propionamide, trifluoroacetate IS-MS, calcd. m/z for $C_{28}H_{38}N_4O_2$ [M+H$^+$]$^+$: 463.3; obsd. 463.0.

Example 18

3-[2,4-dimethyl-5-(2-oxo-1,2-dihydro-indol-3-ylidenemethyl)-1H-pyrrol-3-yl]-N-methyl-N-[2'-methylaminomethylbiphen-2-ylmethyl]propionamide, trifluoroacetate IS-MS, calcd. m/z for $C_{34}H_{36}N_4O_2$ [M+H$^+$]$^+$: 533.3; obsd. 533.2.

Example 19

3-[2,4-dimethyl-5-(2-oxo-1,2-dihydro-indol-3-ylidenemethyl)-1H-pyrrol-3-yl]-N-methyl-N-(3-[4-(3-methylaminopropyl)-piperazin-1-yl]propyl)propionamide, trifluoroacetate IS-MS, calcd. m/z for $C_{30}H_{44}N_6O_2$ [M+H$^+$]$^+$: 521.4; obsd. 521.2.

Example 20

3-[3,5-dimethyl-4-(3-oxo-3-piperidin-1-ylpropyl)-1H-pyrrol-2-ylmethylene]-1,3-dihydroindol-2-one, trifluoroacetate IS-MS, calcd. m/z for $C_{23}H_{27}N_3O_2$ [M+H$^+$]$^+$: 378.2; obsd. 378.0.

Example 21

3-[3,5-dimethyl-4-[3-oxo-3-(piperidin-4-ylpropyl)piperidin-1-ylpropyl]-1H-pyrrol-2-ylmethylene]-1,3-dihydroindol-2-one, trifluoroacetate IS-MS, calcd. m/z for $C_{31}H_{42}N_4O_2$ [M+H$^+$]$^+$: 503.3; obsd. 503.2.

Example 22

3-[3,5-dimethyl-4-[3-oxo-3-(4-ethyl)piperazin-1-ylpropyl]-1H-pyrrol-2-ylmethylene]-1,3-dihydroindol-2-one, trifluoroacetate IS-MS, calcd. m/z for $C_{24}H_{30}N_4O_2$ [M+H$^+$]$^+$: 407.2; obsd. 407.0.

Example 23

3-[3,5-dimethyl-4-(3-oxo-3-homopiperazin-1-ylpropyl)-1H-pyrrol-2-ylmethylene]-1,3-dihydroindol-2-one, trifluoroacetate IS-MS, calcd. m/z for $C_{23}H_{28}N_4O_2$ [M+H$^+$]$^+$: 393.2; obsd. 393.0.

Example 24

3-[3,5-dimethyl-4-[3-oxo-3-(1,4,10-trioxa-7,13-diazacyclopentadecan-1-yl)-1H-pyrrol-2-ylmethylene]-1,3-dihydroindol-2-one, trifluoroacetate IS-MS, calcd. m/z for $C_{28}H_{38}N_4O_5$ [M+H$^+$]$^+$: 511.3; obsd. 511.0.

Following the methods of Examples 1a and 2, the following compounds are also prepared:
5-Bromo-3-[3,5-dimethyl-4-[3-oxo-3-(4-prop-2-yl)piperazin-1-ylpropyl]-1H-pyrrol-2-ylmethylene]-1,3-dihydroindol-2-one, trifluoroacetate and
5-bromo-3-[3,5-dimethyl-4-(3-oxo-3-[4-prop-2-yl]homopiperazin-1-ylpropyl)-1H-pyrrol-2-ylmethylene]-1,3-dihydroindol-2-one, trifluoroacetate.

Biological Assays

The ability of test compounds to inhibit receptor tyrosine kinases is demonstrated in the following assays.

| Abbreviations | |
|---|---|
| HEPES | 4-(2-hydroxyethyl)-1-piperazineethanesulfonic acid |
| EDTA | Ethylenediaminetetraacetic acid |
| PDGF | Platelet Derived Growth Factor |
| PDGFR | Platelet Derived Growth Factor Receptor |
| VEGF | Vascular Endothelial Growth Factor |
| VEGFR | Vascular Endothelial Growth Factor Receptor |
| HEK cells | Human Embryonic Kidney cells |
| Flt-3 | fms-related tyrosine kinase 3 |
| BSA | Bovine Serum Albumin |
| AML | Acute Myeloid Leukemia |
| ITD | Internal Tandem Duplication |
| MTT | 3-(4,5-dimethylthiazol-2-yl)-2,5-diphenyl tetrazolium bromide. |
| HUVEC | Human umbilical vein epithelial cells |

Ca$^{2+}$ Release Assay (FLIPR Assay)

The binding of growth factors to their respective receptors leads to the autophosphorylation of the receptor. This is the first step in a signaling cascade that results in the release of Ca$^{2+}$ from internal stores and influx of extracellular Ca$^{2+}$.

The rise in intracelluar Ca$^{2+}$ is quantitated by loading cells with a fluorescent dye prior to stimulation with the growth factor and by subsequently assessing the fluorescent signal in a Fluorometric Image Plate Reader (FLIPR). A kinase inhibitor that can penetrate the cell membrane inhibits receptor autophosphorylation, hence, the Ca$^{2+}$ release is reduced or ablated.

In order to determine the IC$_{50}$ of test compounds against the VEGFR in the FLIPR assay, HUVECs (Walkersville, Md.) were used. For the determination of IC$_{50}$s against the PDGFR, a HEK cell line were used that expresses the human PDGFR. 40–50000 cells per well were plated in a 96 well plate. The cells were incubated for 3–4 hours to adhere to the plate. Subsequently, the cells were washed twice in FLIPR buffer (1×HBS, 2 mM CaCl, 10 mM HEPES, pH7.4, 2.5 mM Probenecid, 0.1% BSA). After the second wash 50 μL of the Ca$^{2+}$ sensitive dye FLUO-3 (FLUO-3 (AM) TEF Labs, 50 μg in 10 mL FLIPR buffer) was added to the remaining 50 μL buffer in each well. After loading the cells for one hour, the cells were washed twice and the test compounds were added in 50 µL as a 2x solution to the 50 µL of buffer in each well. The cells were incubated with the compounds for 30 minutes and then VEGF (40 ng/mL, BioSource International) for the VEGFR or PDGF (40 ng/mL, BioSource International) for the PDGFR was added. The change in fluorescence intensity was measured in a Fluorometric Image Plate Reader (FLIPR) (Molecular Devices).

Proliferation and Viability Assay (MTT)

The inhibition of mutant Flt-3 ITD is expected to affect the proliferation and viability of AML cells with this mutation. In order to assess the activity of test compounds an MTT proliferation and viability assay (Roche Molecular Biochemicals, Indianapolis, Ind.) was performed with an AML cell line called MV4-11. MV4-11 cells express Flt-3 ITD. 50,000 cells per well in 100 µL of media were plated in a 96 well plate and were incubated with increasing concentrations of compound for 48 hours. After this incubation period, 10 µL of the MTT labeling reaction was added for 4 hours. The MTT labeling reagent was metabolized by viable cells to formazan, an insoluble blue salt. To solubilize the formazan salt, 100 µL of solubilization solution was added. The plate was incubated at 37 degrees Celsius for 24 hours and, then, the optical density of the wells was determined spectrophotometrically at 550 nm. The optical density of the solutions in the wells reflects the effect the compound has on the viability of the cells.

Immunoprecipitation/Western (IP/Western)

The binding of growth factors to receptor tyrosine kinases like Flt-3 or PDGFR leads to the autophosphorylation of the receptors. The inhibition of autophosphorylation is the objective pursued with kinase inhibitors. By performing an IP/Western experiment the level of receptor autophosphorylation can be assessed directly.

$5 \times 10^6$ cells (HEK PDGFR cell line for PDGFR, HEK c-Kit for c-Kit, and THP-1, HL-60 or MV4-11 for Flt-3) were incubated for 30 minutes in 2.5 mL of culture media with a defined concentration of test compound. In order to stimulate receptor autophosphorylation, growth factor (PDGF, SCF, or Flt-3 ligand respectively, 50 ng/mL, Biosource International, Camarillo, Calif.) was added for 5 minutes. The cells were then centrifuged and lysed in 500 µL lysis buffer (50 mM Tris pH 7.4, 1% NP-40, 150 mM NaCl, 1 mM EDTA, 1 mM Na3VO4). The lysate is centrifuged and 10 µL of antibody against the respective receptor was added to the supernatant (anti-PDGFR (P20), anti-c-Kit (C-19), and anti-Flt-3 (S18), Santa Cruz Biotechnology, Inc.). The immunocomplexes were isolated with Protein G beads (Sigma, St. Louis, Mo.) and PAGE was performed. A Western Blot was done using an antibody against phosphotyrosine residues (4G10, Upstate Biotechnology, Lake Placid, N.Y.). The intensity of the phospho-tyrosine signal corresponding to various drug concentrations provides a way to determine the $IC_{50}$ of the test compound for the inhibition of autophosphorylation.

In general, the compounds exemplified herein have been found to exhibit an $IC_{50}$ of less than 10 µM in one or more of the above assays.

Pharmacokinetics

To evaluate pharmacokinetics, male Sprague Dawley rats (CD strain, Charles River Laboratories, Wilmington, Mass.) were dosed with test compounds via intravenous (IV) administration, at 1 mg/kg concentration, and oral (PO) administration, at 10 mg/kg concentration. Blood samples were collected from animals pre-dose, and at 2, 5, 15, and 30 minutes, and at 1, 2, 4, 6, 8, and 24 hours post-dose. Plasma concentrations were determined by liquid chromatography-mass spectrometry (LC-MS) (MDS SCIEX API 4000, Applied Biosystems, Foster City, Calif.). Standard pharmacokinetic parameters were assessed by non-compartmental methods using the WinNonlin Version 3.2 software package (Pharsight, Mountain View, Calif.). Oral bioavailability was determined as the ratio of the area under the curve (AUC) in the graph of plasma concentration versus time for PO administration to the corresponding quantity for IV administration. The oral bioavailability in rats, for example, of 3-[3,5-dimethyl-4-(3-oxo-3-piperazin-1-ylpropyl)-1H-pyrrol-2-ylmethylene]-1,3-dihydroindol-2-one, determined by this method, was 50.6%.

Comparative Assay Results

Table 1 lists assay results for two compounds of the invention, the compound of Example 1,3-[3,5-dimethyl-4-(3-oxo-3-piperazin-1-yl-propyl)-1H-pyrrol-2-ylmethylene]-1,3-dihydroindol-2-one, trifluoroacetate, and the compound of Example 22, 3-[3,5-dimethyl-4-[3-oxo-3-(4-ethyl)piperazin-1-ylpropyl]-1H-pyrrol-2-ylmethylene]-1,3-dihydroindol-2-one, trifluoroacetate. For comparison, Table 1 also lists assay results for two prior art compounds, 3-[2,4-dimethyl-5-(2-oxo-1,2-dihydroindol-3-ylidenemethyl)-1H-pyrrol-3-yl]propionic acid, identified as SU6668, and 3-(2,3-dimethylpyrrol-5-yl)methylene]-2-indolinone, identified as SU5416. The preparation of the former prior art compound is described above as intermediate 9. The latter compound was prepared as described in Sun et al., *J. Med. Chem.* 1998, Vol. 41, No. 14, pp 2588–2603. The ability of test compounds to inhibit mutant Flt-3 ITD was tested in the cytotoxicity assay. Inhibition of the VEGFR and PDGFR kinases was tested in the $Ca^{2+}$ FLIPR assay, except as indicated. As shown below the compounds of Examples 1 and 22 showed sub-micromolar activity in the Flt-3, VEGFR, and PDGFR assays.

TABLE 1

| | Flt-3 $EC_{50}$ (µM) | VEGFR $IC_{50}$ (µM) | PDGFR $IC_{50}$ (µM) |
|---|---|---|---|
| This Invention | | | |
| Example 1 | 0.24 | 0.02 | 0.03# |
| Example 22 | 0.22 | 0.03 | 0.09 |
| Comparison Compounds | | | |
| SU6668 | No activity* | No activity** | No activity**# |
| SU5416 | ~1–10 | 0.05 | 0.06 |

*Highest concentration tested 10 µm
**Highest concentration tested 1 µm
Immunoprecipitation/Western (IP) assay

The invention claimed is:

1. A method of treating a condition responsive to a tyrosine kinase inhibitor, wherein the condition is selected from acute myeloid leukemia, small cell lung cancer, prostate cancer, gastrointestinal cancer, breast cancer, brain cancer, and restenosis, the method comprising administering to a patient in need of treatment a therapeutically-effective amount of a compound of formula (Ia):

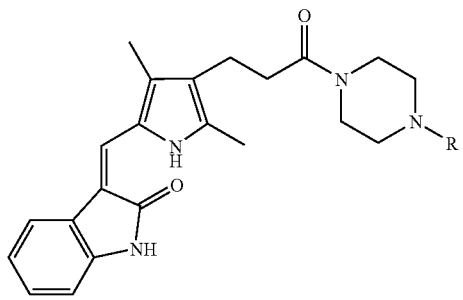

wherein R is hydrogen, methyl or ethyl;
or a pharmaceutically-acceptable salt thereof.

2. The method of claim 1, wherein the compound is selected from the group consisting of:
  3-[3,5-dimethyl-4-(3-oxo-3-piperazin-1-ylpropyl)-1H-pyrrol-2-ylmethylene]-1,3-dihydroindol-2-one,
  3-[3,5-dimethyl-4-[3-oxo-3-(4-ethyl)piperazin-1-ylpropyl]-1H-pyrrol-2-ylmethylene]-1,3-dihydroindol-2-one,
  and pharmaceutically-acceptable salts thereof.

3. The method of claim 1 wherein the compound is 3-[3,5-dimethyl-4-(3-oxo-3-piperazin-1-ylpropyl)-1H-pyrrol-2-ylmethylene]-1,3-dihydroindol-2-one or a pharmaceutically-acceptable salt thereof.

4. A method of treating a condition responsive to a tyrosine kinase inhibitor, wherein the condition is selected from acute myeloid leukemia, small cell lung cancer, prostate cancer, gastrointestinal cancer, breast cancer, brain cancer, and restenosis, the method comprising administering to a patient in need of treatment a therapeutically-effective amount of a pharmaceutical composition comprising a pharmaceutically acceptable diluent or carrier and a compound of formula (Ia):

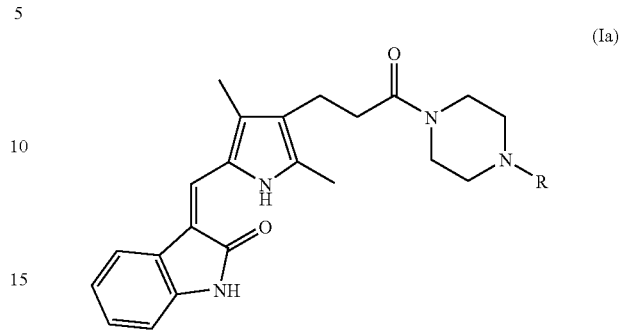

wherein R is hydrogen, methyl, or ethyl,
or a pharmaceutically-acceptable salt thereof.

5. The method of claim 4, wherein the compound is selected from the group consisting of:
  3-[3,5-dimethyl-4-(3-oxo-3-piperazin-1-ylpropyl)-1H-pyrrol-2-ylmethylene]-1,3-dihydroindol-2-one,
  3-[3,5-dimethyl-4-[3-oxo-3-(4-ethyl)piperazin-1-ylpropyl]-1H-pyrrol-2-ylmethylene]-1,3-dihydroindol-2-one,
  and pharmaceutically-acceptable salts thereof.

6. The method of claim 4 wherein the compound is 3-[3,5-dimethyl-4-(3-oxo-3-piperazin-1-ylpropyl)-1H-pyrrol-2-ylmethylene]-1,3-dihydroindol-2-one or a pharmaceutically-acceptable salt thereof.

* * * * *